US007041649B2

(12) United States Patent
Schiell et al.

(10) Patent No.: US 7,041,649 B2
(45) Date of Patent: May 9, 2006

(54) METHOD FOR TREATING NEUROLOGICAL CONDITIONS AND INDUCING IMMUNOSUPPRESSION WITH CEPHAIBOLS

(75) Inventors: Mathias Schiell, Brechen (DE); Laszio Vertesy, Eppstein-Vockenhausen (DE); Joachim Wink, Rodermark (DE); Brigitte Schlegel, Jena (DE); Albert Haertl, Jena (DE); Udo Graefe, Jena (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 0 days.

(21) Appl. No.: 10/442,848

(22) Filed: May 21, 2003

(65) Prior Publication Data

US 2004/0023886 A1 Feb. 5, 2004

Related U.S. Application Data

(60) Provisional application No. 60/395,011, filed on Jul. 11, 2002.

(30) Foreign Application Priority Data

May 23, 2002 (DE) .............................. 102 22 792

(51) Int. Cl.
*A61K 38/10* (2006.01)
(52) U.S. Cl. .......................... 514/13; 514/14
(58) Field of Classification Search .................. 514/13, 514/14; 530/326
See application file for complete search history.

(56) References Cited

U.S. PATENT DOCUMENTS 6,582,949 B1    6/2003    Vértesy ....................... 435/243

FOREIGN PATENT DOCUMENTS

| DE | 197 40 030 | 3/1999 |
|----|-----------|--------|
| DE | 199 48 644 | 4/2001 |
| WO | WO 99/12958 | 3/1999 |
| WO | WO 00/68256 | 11/2000 |

OTHER PUBLICATIONS

Argoudelis A.D. et al., Emerimicins II, III, And IV, Antibiotics Produced By *Emericellopsis microspora* In Media Supplemented With Trans-4-n-Propyl-l-Proline, The Journal Of Antibiotics, (1974), vol. 27, pp. 274-282.
Argoudelis A.D. et al., Zervamicins* I And II, Polypeptide Antibiotics Produced By *Emericellopsis salmosynnemata*, The Journal Of Antibiotics, (1974), vol. 27, No. 5, pp. 321-328.
Bennett John V. et al., Simplied, Accurate Method For Antibiotic Assay Of Clinical Specimens, Applied Microbiology, (1966), vol. 14, No. 2, pp. 170-177.

Berg Albrecht et al., Isolation And Structural Elucidation Of New Peptaibols, Bergofungins B, C And D, From *Emericellopsis donezkii* HKI 0059, The Journal Of Antibiotics, (1999), vol. 52, No. 7. pp. 666-669.
Bruckner Hans et al., The Sequences Of The Membrane-Modifying Peptide Antibiotic Trichotoxin A-40, Angew. Chem. Int. Ed. Engl., (1979), vol. 18, No. 6, pp. 476-477.
Bunggaard Hans et al., A Novel Solution-Stable, Water-Soluble Prodrug Type For Drugs Containing A Hydroxyl Or An NH-Acidic Group, Journal Of Medicinal Chemistry, (1989), vol. 32, No. 12, pp. 2503-2507.
Chikanishi Toshihiro et al., Clonostachin, A Novel Peptaibol That Inhibits Platelet Aggregation, The Journal Of Antibiotics, (1997), vol. 50, No. 2, pp. 105-110.
Council Of Europe Biological Assays, European Pharmacopoeia, Third Edition, European Treaty Series No. 50 (not dated).
Das Manoj K. et al., Membrane Channel Forming Polypeptides. Molecular Conformation And Mitochondrial Uncoupling Activity Of Antiamoebin, An Alpha-Aminoisobutyric Acid Containing Peptide, Biochemistry, (1986), vol. 25, pp. 7110-7117.
Dornberger Klausjurgen et al., Chrysospermins, New Peptaibol Antibiotics From *Apiocera chrysoperma* Ap101, The Journal Of Antibiotics, (1995), vol. 48, No. 9, pp. 977-989.
Jaworski Andreas et al., New Sequences And New Fungal Producers Of Peptaibol Antibiotics Antiamoebins, Journal Of Peptide Science, (2000), vol. 6, pp. 149-167.
Kronen Matthias et al., Ampullosporins, B, C, D, E1, E2, E3, And E4 From *Sepedonium ampullosporum* HKI-0053: Structures And Biological Activities, The Journal Of Antibiotics, (2001), vol. 54, No. 2, pp. 175-178.
Kumazawa Shigenori, Structural Elucidation of Aibellin, A New Peptide Antibiotic With Efficiency Enhancing Activity On Rumen Fermentation, The Journal Of Antibiotics, (1994), vol. 47, No. 10, pp. 1136-1144.
Nagaraj G. et al., Antimalarial Activities Of Peptide Antibiotics Isolated From Fungi, Antimicrobial Agents And Chemotherapy, (2001), vol. 45, No. 1, pp. 145-149.
Rinehart, Jr. Kenneth L., Fast Atom Bombardment Mass Spectrometry; A Promising Tool For Structural Studies, Trends In Analytical Chemistry, (1989), vol. 2, No. 1, pp. 10-14.
Ritzau Michael et al., Ampullosporin, A New Peptailbol-Type Antibiotic From *Sepedonium ampullosporum* HKI-0053 With Neuroleptic Activity In Mice, The Journal Of Antibiotics, (1997), pp. 722-728.

(Continued)

Primary Examiner—Jeffrey Edwin Russel
(74) Attorney, Agent, or Firm—Ann Marie Szczepanik

(57) ABSTRACT

Embodiments of the present invention relate to administering cephaibols to treat conditions of the nervous system and to treat those conditions in which suppressing the immune system would have beneficial effect.

71 Claims, No Drawings

OTHER PUBLICATIONS

Sciell Matthias et al., Cephaibols, New Peptaibol Antibiotics With Anthelmintic Properties From *Acremonium tubakii* DSM 12774, The Journal Of Antibiotics, (2001), Vo. 54, No. 3, pp. 220-233.

Sharman Gary J. et al., Structural Elucidation Of XR586, A Peptaibol-Like Antibiotic From *Acremonium persicinum*, Biochemistry Journal, (1996), vol. 320, pp. 723-728.

Snook CF et al., The Structure And Function Of Antiamoebin I, A Proline-Rich Membrance-Active Polypeptide Structure, (1998), vol. 6, pp. 783-792.

Yun Bong-Sik et al., Peptaivirins A and B, Two New Antiviral Peptailbols Against TMV Infection, Tetrahedron Letters, (I2000), Vol. 41, pp. 1429-1431.

Remington's Pharmaceutical Sciences, Remington's Pharmaceutical Sciences, (1985), p. 1418.

Structure Of The Peptide Antibiotic Antiamoebin II, The Journal Of Antibiotics, (1978), vol. 31, No. 3, pp. 241-243.

SEQUENCE LISTING

<160> NUMBER OF SEQ ID NOS: 8

<210> SEQ ID NO 1

<211> LENGTH: 16
<212> TYPE: PRT
<213> ORGANISM: Acremonium tubakii
<220> FEATURE:
<221> NAME/KEY: MOD_RES
<222> LOCATION: (1)
<223> OTHER INFORMATION: AcPhe
<220> FEATURE:
<221> NAME/KEY: MOD_RES
<222> LOCATION: (2)..(5)
<223> OTHER INFORMATION: Aib
<220> FEATURE:
<221> NAME/KEY: MOD_RES
<222> LOCATION: (8)
<223> OTHER INFORMATION: Iva
<220> FEATURE:
<221> NAME/KEY: MOD_RES
<222> LOCATION: (9)
<223> OTHER INFORMATION: Aib
<220> FEATURE:
<221> NAME/KEY: MOD_RES
<222> LOCATION: (10)
<223> OTHER INFORMATION: Hyp
<220> FEATURE:
<221> NAME/KEY: MOD_RES
<222> LOCATION: (12)
<223> OTHER INFORMATION: Iva
<220> FEATURE:
<221> NAME/KEY: MOD_RES
<222> LOCATION: (13)
<223> OTHER INFORMATION: Hyp
<220> FEATURE:
<221> NAME/KEY: MOD_RES
<222> LOCATION: (14)
<223> OTHER INFORMATION: Aib
<220> FEATURE:
<221> NAME/KEY: MOD_RES
<222> LOCATION: (16)
<223> OTHER INFORMATION: Phe-ol

<400> SEQUENCE: 1

Xaa Xaa Xaa Xaa Xaa Gly Leu Xaa Xaa Xaa Gln Xaa Xaa Xaa Pro Xaa
1               5                   10                  15

<210> SEQ ID NO 2
<211> LENGTH: 16
<212> TYPE: PRT
<213> ORGANISM: Acremonium tubakii
<220> FEATURE:
<221> NAME/KEY: MOD_RES
<222> LOCATION: (1)
<223> OTHER INFORMATION: AcPhe
<220> FEATURE:
<221> NAME/KEY: MOD_RES
<222> LOCATION: (2)..(5)
<223> OTHER INFORMATION: Aib
<220> FEATURE:
<221> NAME/KEY: MOD_RES
<222> LOCATION: (8)
<223> OTHER INFORMATION: Iva
<220> FEATURE:
<221> NAME/KEY: MOD_RES
<222> LOCATION: (9)
<223> OTHER INFORMATION: Aib
<220> FEATURE:
<221> NAME/KEY: MOD_RES
<222> LOCATION: (10)
<223> OTHER INFORMATION: Hyp
<220> FEATURE:
<221> NAME/KEY: MOD_RES
<222> LOCATION: (12)
<223> OTHER INFORMATION: Iva
<220> FEATURE:
<221> NAME/KEY: MOD_RES
<222> LOCATION: (13)
<223> OTHER INFORMATION: Hyp
<220> FEATURE:

```
<221> NAME/KEY: MOD_RES
<222> LOCATION: (14)
<223> OTHER INFORMATION: Aib
<220> FEATURE:
<221> NAME/KEY: MOD_RES
<222> LOCATION: (16)
<223> OTHER INFORMATION: Phe-ol

<400> SEQUENCE: 2

Xaa Xaa Xaa Xaa Xaa Ala Leu Xaa Xaa Xaa Gln Xaa Xaa Xaa Pro Xaa
 1               5                  10                  15

<210> SEQ ID NO 3
<211> LENGTH: 16
<212> TYPE: PRT
<213> ORGANISM: Acremonium tubakii
<220> FEATURE:
<221> NAME/KEY: MOD_RES
<222> LOCATION: (1)
<223> OTHER INFORMATION: AcPhe
<220> FEATURE:
<221> NAME/KEY: MOD_RES
<222> LOCATION: (2)..(4)
<223> OTHER INFORMATION: Aib
<220> FEATURE:
<221> NAME/KEY: MOD_RES
<222> LOCATION: (5)..(5)
<223> OTHER INFORMATION: Iva
<220> FEATURE:
<221> NAME/KEY: MOD_RES
<222> LOCATION: (8)
<223> OTHER INFORMATION: Iva
<220> FEATURE:
<221> NAME/KEY: MOD_RES
<222> LOCATION: (9)
<223> OTHER INFORMATION: Aib
<220> FEATURE:
<221> NAME/KEY: MOD_RES
<222> LOCATION: (10)
<223> OTHER INFORMATION: Hyp
<220> FEATURE:
<221> NAME/KEY: MOD_RES
<222> LOCATION: (12)
<223> OTHER INFORMATION: Iva
<220> FEATURE:
<221> NAME/KEY: MOD_RES
<222> LOCATION: (13)
<223> OTHER INFORMATION: Hyp
<220> FEATURE:
<221> NAME/KEY: MOD_RES
<222> LOCATION: (14)
<223> OTHER INFORMATION: Aib
<220> FEATURE:
<221> NAME/KEY: MOD_RES
<222> LOCATION: (16)
<223> OTHER INFORMATION: Phe-ol

<400> SEQUENCE: 3

Xaa Xaa Xaa Xaa Xaa Gly Leu Xaa Xaa Xaa Gln Xaa Xaa Xaa Pro Xaa
 1               5                  10                  15

<210> SEQ ID NO 4
<211> LENGTH: 16
<212> TYPE: PRT
<213> ORGANISM: Acremonium tubakii
<220> FEATURE:
<221> NAME/KEY: MOD_RES
<222> LOCATION: (1)
<223> OTHER INFORMATION: AcPhe
<220> FEATURE:
<221> NAME/KEY: MOD_RES
<222> LOCATION: (2)..(5)
<223> OTHER INFORMATION: Aib
<220> FEATURE:
<221> NAME/KEY: MOD_RES
```

```
<222> LOCATION: (8)
<223> OTHER INFORMATION: Iva
<220> FEATURE:
<221> NAME/KEY: MOD_RES
<222> LOCATION: (9)
<223> OTHER INFORMATION: Aib
<220> FEATURE:
<221> NAME/KEY: MOD_RES
<222> LOCATION: (10)
<223> OTHER INFORMATION: Hyp
<220> FEATURE:
<221> NAME/KEY: MOD_RES
<222> LOCATION: (12)
<223> OTHER INFORMATION: Aib
<220> FEATURE:
<221> NAME/KEY: MOD_RES
<222> LOCATION: (13)
<223> OTHER INFORMATION: Hyp
<220> FEATURE:
<221> NAME/KEY: MOD_RES
<222> LOCATION: (14)
<223> OTHER INFORMATION: Aib
<220> FEATURE:
<221> NAME/KEY: MOD_RES
<222> LOCATION: (16)
<223> OTHER INFORMATION: Phe-ol

<400> SEQUENCE: 4

Xaa Xaa Xaa Xaa Xaa Gly Leu Xaa Xaa Xaa Gln Xaa Xaa Xaa Pro Xaa
1               5                   10                  15

<210> SEQ ID NO 5
<211> LENGTH: 16
<212> TYPE: PRT
<213> ORGANISM: Acremonium tubakii
<220> FEATURE:
<221> NAME/KEY: MOD_RES
<222> LOCATION: (1)
<223> OTHER INFORMATION: AcPhe
<220> FEATURE:
<221> NAME/KEY: MOD_RES
<222> LOCATION: (2)..(5)
<223> OTHER INFORMATION: Aib
<220> FEATURE:
<221> NAME/KEY: MOD_RES
<222> LOCATION: (8)..(9)
<223> OTHER INFORMATION: Aib
<220> FEATURE:
<221> NAME/KEY: MOD_RES
<222> LOCATION: (10)
<223> OTHER INFORMATION: Hyp
<220> FEATURE:
<221> NAME/KEY: MOD_RES
<222> LOCATION: (12)
<223> OTHER INFORMATION: Aib
<220> FEATURE:
<221> NAME/KEY: MOD_RES
<222> LOCATION: (13)
<223> OTHER INFORMATION: Hyp
<220> FEATURE:
<221> NAME/KEY: MOD_RES
<222> LOCATION: (14)
<223> OTHER INFORMATION: Aib
<220> FEATURE:
<221> NAME/KEY: MOD_RES
<222> LOCATION: (16)
<223> OTHER INFORMATION: Phe-ol

<400> SEQUENCE: 5

Xaa Xaa Xaa Xaa Xaa Gly Leu Xaa Xaa Xaa Gln Xaa Xaa Xaa Pro Xaa
1               5                   10                  15

<210> SEQ ID NO 6
<211> LENGTH: 16
<212> TYPE: PRT
```

```
<213> ORGANISM: Acremonium tubakii
<220> FEATURE:
<221> NAME/KEY: MOD_RES
<222> LOCATION: (1)
<223> OTHER INFORMATION: AcPhe
<220> FEATURE:
<221> NAME/KEY: MOD_RES
<222> LOCATION: (2)..(5)
<223> OTHER INFORMATION: Aib
<220> FEATURE:
<221> NAME/KEY: MOD_RES
<222> LOCATION: (8)..(9)
<223> OTHER INFORMATION: Aib
<220> FEATURE:
<221> NAME/KEY: MOD_RES
<222> LOCATION: (10)
<223> OTHER INFORMATION: Hyp
<220> FEATURE:
<221> NAME/KEY: MOD_RES
<222> LOCATION: (12)
<223> OTHER INFORMATION: Iva
<220> FEATURE:
<221> NAME/KEY: MOD_RES
<222> LOCATION: (13)
<223> OTHER INFORMATION: Hyp
<220> FEATURE:
<221> NAME/KEY: MOD_RES
<222> LOCATION: (14)
<223> OTHER INFORMATION: Aib
<220> FEATURE:
<221> NAME/KEY: MOD_RES
<222> LOCATION: (16)
<223> OTHER INFORMATION: Phe-ol

<400> SEQUENCE: 6

Xaa Xaa Xaa Xaa Xaa Gly Leu Xaa Xaa Xaa Gln Xaa Xaa Xaa Pro Xaa
1               5                   10                  15

<210> SEQ ID NO 7
<211> LENGTH: 17
<212> TYPE: PRT
<213> ORGANISM: Acremonium tubakii
<220> FEATURE:
<221> NAME/KEY: MOD_RES
<222> LOCATION: (1)
<223> OTHER INFORMATION: AcPhe
<220> FEATURE:
<221> NAME/KEY: MOD_RES
<222> LOCATION: (2)
<223> OTHER INFORMATION: Iva
<220> FEATURE:
<221> NAME/KEY: MOD_RES
<222> LOCATION: (4)
<223> OTHER INFORMATION: Aib
<220> FEATURE:
<221> NAME/KEY: MOD_RES
<222> LOCATION: (7)
<223> OTHER INFORMATION: Aib
<220> FEATURE:
<221> NAME/KEY: MOD_RES
<222> LOCATION: (9)
<223> OTHER INFORMATION: Aib
<220> FEATURE:
<221> NAME/KEY: MOD_RES
<222> LOCATION: (10)
<223> OTHER INFORMATION: Hyp
<220> FEATURE:
<221> NAME/KEY: MOD_RES
<222> LOCATION: (12)
<223> OTHER INFORMATION: Aib
<220> FEATURE:
<221> NAME/KEY: MOD_RES
<222> LOCATION: (13)
<223> OTHER INFORMATION: Hyp
<220> FEATURE:
<221> NAME/KEY: MOD_RES
<222> LOCATION: (14)
```

-continued

```
<223> OTHER INFORMATION: Aib

<400> SEQUENCE: 7

Xaa Xaa Gln Xaa Ile Thr Xaa Leu Xaa Xaa Gln Xaa Xaa Xaa Pro Phe
1               5                   10                  15
Ser

<210> SEQ ID NO 8
<211> LENGTH: 17
<212> TYPE: PRT
<213> ORGANISM: Acremonium tubakii
<220> FEATURE:
<221> NAME/KEY: MOD_RES
<222> LOCATION: (1)
<223> OTHER INFORMATION: AcPhe
<220> FEATURE:
<221> NAME/KEY: MOD_RES
<222> LOCATION: (2)
<223> OTHER INFORMATION: Iva
<220> FEATURE:
<221> NAME/KEY: MOD_RES
<222> LOCATION: (4)
<223> OTHER INFORMATION: Aib
<220> FEATURE:
<221> NAME/KEY: MOD_RES
<222> LOCATION: (7)
<223> OTHER INFORMATION: Aib
<220> FEATURE:
<221> NAME/KEY: MOD_RES
<222> LOCATION: (9)
<223> OTHER INFORMATION: Aib
<220> FEATURE:
<221> NAME/KEY: MOD_RES
<222> LOCATION: (12)
<223> OTHER INFORMATION: Aib
<220> FEATURE:
<221> NAME/KEY: MOD_RES
<222> LOCATION: (13)
<223> OTHER INFORMATION: Hyp
<220> FEATURE:
<221> NAME/KEY: MOD_RES
<222> LOCATION: (14)
<223> OTHER INFORMATION: Aib

<400> SEQUENCE: 8

Xaa Xaa Gln Xaa Ile Thr Xaa Leu Xaa Pro Gln Xaa Xaa Xaa Pro Phe
1               5                   10                  15
Ser
```

METHOD FOR TREATING NEUROLOGICAL CONDITIONS AND INDUCING IMMUNOSUPPRESSION WITH CEPHAIBOLS

This application claims the benefit of priority under 35 U.S.C. § 119(a)–(d) of German Application No. 10222792.6 filed on May 23, 2002, and of U.S. Provisional Application No. 60/395,011 filed on Jul. 11, 2002, the contents of both of which are hereby incorporated by reference.

FIELD OF THE INVENTION

Embodiments of the present invention relate to methods for treating conditions of the nervous system and those conditions in which suppressing the immune system would have beneficial effect.

BACKGROUND OF THE INVENTION

Peptides containing up to 20 amino acids, some of which are structurally unusual, are produced by bacteria and fungi by way of their secondary metabolism using non ribosomal peptide synthetases. Many of the secondary metabolites having a peptide structure which are thus far known possess interesting biological effects as antibiotics, enzyme inhibitors, cardiotonics, immunomodulators, insecticides, nematocides, etc. (see, for example, Grafe, U. Biochemie der Antibiotika (Biochemistry of the Antibiotics), Spektrum Heidelberg, 1992).

Within the structural class of the peptide active compounds, what are termed the peptaibols are distinguished by the fact that they contain an unusually large number of amino acids (up to 20) including a high proportion of alpha-aminobutyric acid (Brückner, H., König, W. A., Greiner, M., Jung, G. Angew. Chem. Int. Ed. Engl. 18 (1979), 476–477). Furthermore, peptaibols are frequently acetylated at the N terminus and have a residue containing an alcohol group (e.g. phenylalaninol) or an aldehyde group at the C terminus.

The mode of action of the peptaibols is generally assumed to be the formation of pores in biological membranes (M. K. Das et al., Biochemistry, 25, 7110–7117, 1986). As a result, ions can penetrate into the cell in an uncontrolled manner and interfere with the vital biochemical processes, something which could explain the antibiotic effect of many peptaibols. In addition to the antibiotic effect, various peptaibols have been observed to have other biological effects which are different. Ampullosporins induce pigment formation in *Phoma destructiva* and produce neuroleptic effects in the mouse (WO99/12598; DE199148644; M. Ritzau et al. J. Antibiotics 50, 722–728,1997; Kronen et al., J. Antibiotics, 54,175–178,2001). While bergofungin components (A. Berg et al. J. Antibiotics 52, 666–669, 1999) inhibit prolylendopeptidase in submicromolar concentrations, they have no effects on *Phoma destructiva*. Clonostachin (T. Chikanishi et al, J. Antibiotics, 50, 105–110, 1997) inhibits platelet aggregation. The antiviral peptaivirins A and B (B. S. Yun et al. Tetrahedron Letters, 41, 1429–1431,2000) have recently been described. It is not possible to provide any uniform explanation for, and prediction of, the biological activities of the various peptaibols because of the differences in the structures of these compounds.

The cephaibols, which are composed linearly of 16 or 17 amino acids or amino acid derivatives, some of which are not encodable, constitute another group of the peptaibol antibiotics. The structure, preparation and biological activities of the cephaibols are described, for example, in WO 00/68256 or M. Schiell et al., J. Antibiotics, 54 (2001) 220–233. Cephaibols have inhibitory effects on endoparasites and/or ectoparasites (as described in U.S. Pat. No. 6,582,949) which are pathogenic to humans and/or animals, such as trematodes, nematodes, arachnida and some insects. In addition to this, the cephaibols exhibit antibacterial activities.

Cephaibols are not known to have any other therapeutic uses.

DETAILED DESCRIPTION OF THE INVENTION

The inventors have surprisingly discovered that cephaibols may be used to treat conditions of the nervous system and to treat those conditions for which suppressing an immune response would be beneficial.

In one embodiment, the invention comprises a method of treating a condition of the nervous system by administering to a mammal compounds of Formula I:

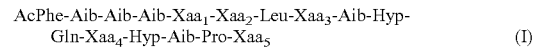

wherein $Xaa_5$ is Phe-ol or Phe-al, and $Xaa_1$, $Xaa_2$, $Xaa_3$, and $Xaa_4$ are as follows:
a) $Xaa_1$ is Aib, $Xaa_2$ is Gly or Ala, and $Xaa_3$ and $Xaa_4$ are Iva;
b) $Xaa_1$ is Iva, $Xaa_2$ is Gly, and $Xaa_3$ and $Xaa_4$ are Iva;
c) $Xaa_1$ is Aib, $Xaa_2$ is Gly, $Xaa_3$ is Iva, and $Xaa_4$ is Aib;
d) $Xaa_1$ is Aib, $Xaa_2$ is Gly, and $Xaa_3$ and $Xaa_4$ are Aib; or
e) $Xaa_1$ is Aib, $Xaa_2$ is Gly, $Xaa_3$ is Aib and $Xaa_4$ is Iva;

or compounds of Formula II:

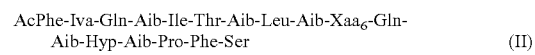

wherein $Xaa_6$ is Hyp or Pro, or pharmaceutically acceptable salts of such compounds.

In another embodiment, the invention comprises a method of suppressing an immune response by administering to a mammal compounds of Formulas I or II, where $Xaa_1$–$Xaa_6$ are as defined above, or pharmaceutically acceptable salts of such compounds.

The amino acids of Formulas I and II are abbreviated as follows:

TABLE I

Amino acid abbreviations

| ABBREVIATION | AMINO ACID |
| --- | --- |
| AcPhe | N-Acetylphenylalanine |
| Aib | α-Aminoisobutyric acid |
| Gln | Glutamine |
| Gly | Glycine |
| Hyp | Hydroxyproline |
| Ile | Isoleucine |
| Iva | Isovaline |
| Leu | Leucine |
| Phe | Phenylalanine |
| Phe-al | Phenylalanilal |
| Phe-ol | Phenylalanilol |
| Pro | Proline |
| Ser | Serine |
| Thr | Threonine |

Compounds of the Formulas I or II are also known as peptide active compounds or cephaibols. These include cephaibols A, A1, B, C, D, E, P, and Q.

Cephaibol A denotes a compound of Formula I in which $Xaa_1$ is Aib, $Xaa_2$ is Gly, $Xaa_3$ and $Xaa_4$ are Iva, and $Xaa_5$ is Phe-ol:

AcPhe-Aib-Aib-Aib-Aib-Gly-Leu-Iva-Aib-Hyp-Gln-Iva-Hyp-Aib-Pro-Phe-ol (SEQ ID NO:1)

Cephaibol A

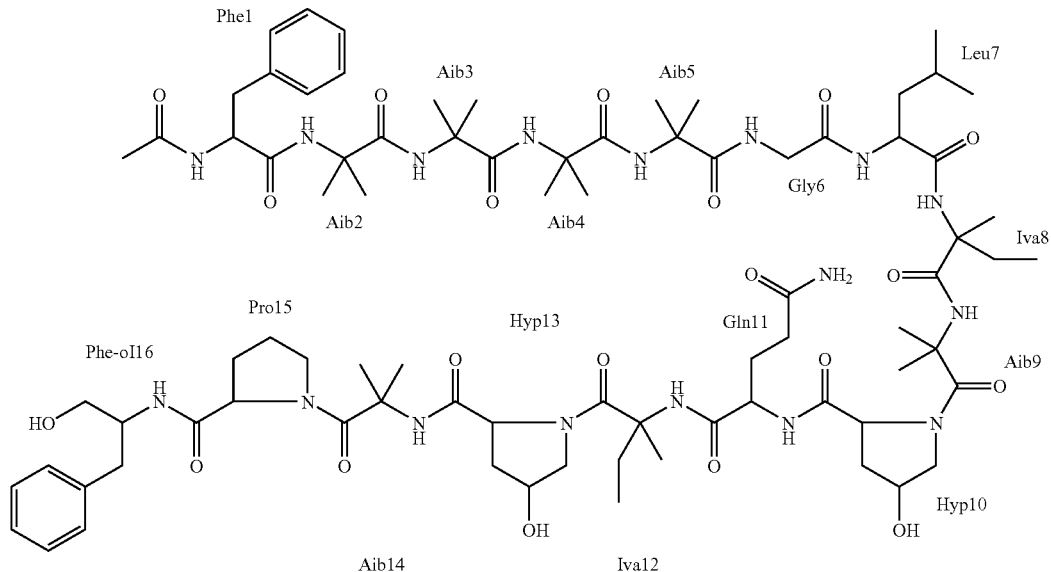

Cephaibol A1 denotes a compound of Formula I in which $Xaa_1$ is Aib, $Xaa_2$ is Ala, $Xaa_3$ and $Xaa_4$ are Iva, and $Xaa_5$ is Phe-ol:

AcPhe-Aib-Aib-Aib-Aib-Ala-Leu-Iva-Aib-Hyp-Gln-Iva-Hyp-Aib-Pro-Phe-ol (SEQ ID NO:2)

Cephaibol A1

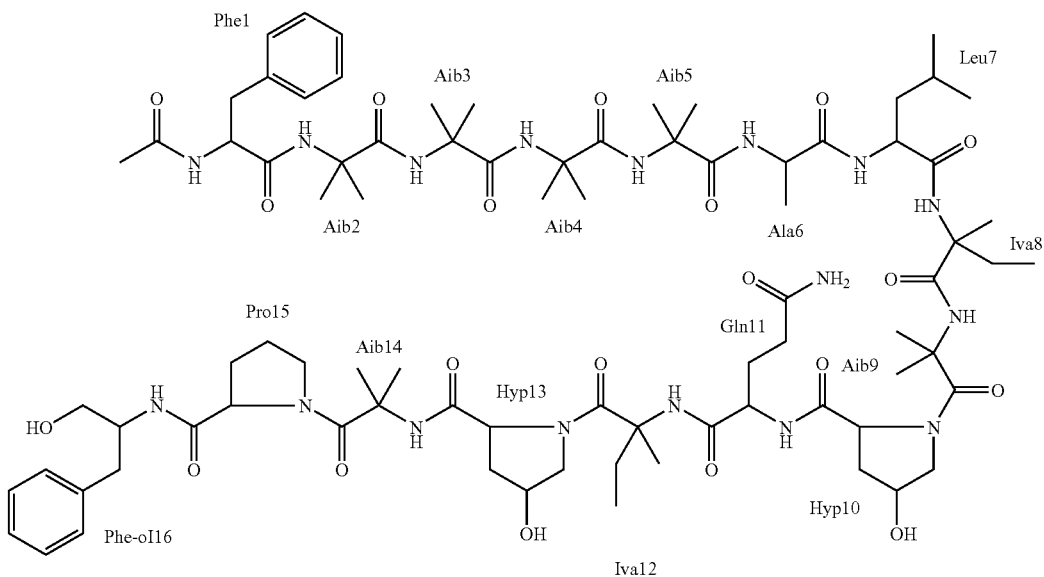

Cephaibol B denotes a compound of Formula I in which Xaa$_1$ is Iva, Xaa$_2$ is Gly, Xaa$_3$ and Xaa$_4$ are Iva, and Xaa$_5$ is Phe-ol:
AcPhe-Aib-Aib-Aib-Iva-Gly-Leu-Iva-Aib-Hyp-Gln-Iva-Hyp-Aib-Pro-Phe-ol (SEQ ID NO:3)

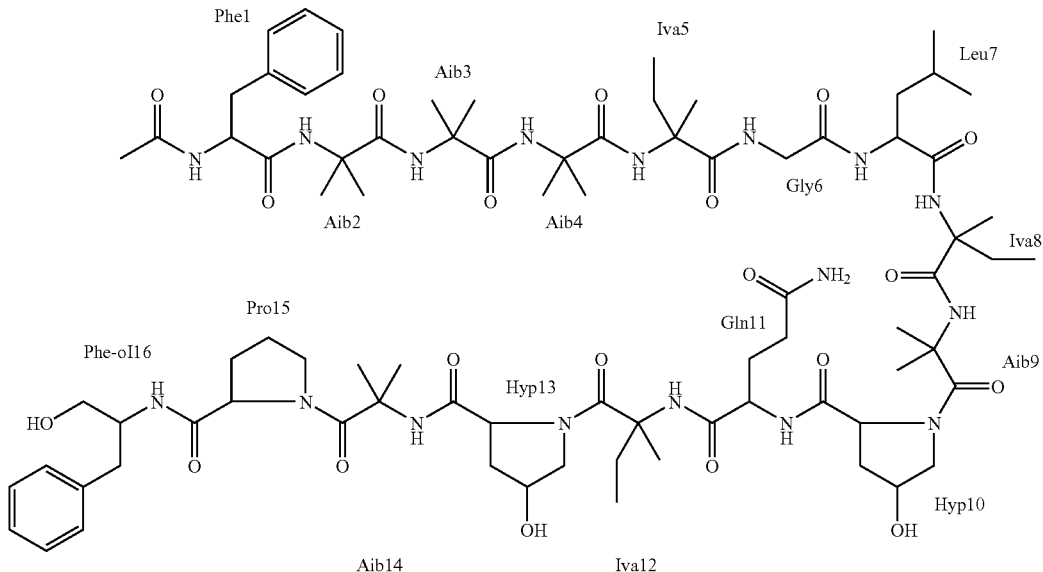

Cephaibol B

Cephaibol C denotes a compound of Formula I in which Xaa$_1$ is Aib, Xaa$_2$ is Gly, Xaa$_3$ is Iva, Xaa$_4$ is Aib, and Xaa$_5$ is Phe-ol:
AcPhe-Aib-Aib-Aib-Aib-Gly-Leu-Iva-Aib-Hyp-Gln-Aib-Hyp-Aib-Pro-Phe-ol (SEQ ID NO:4)

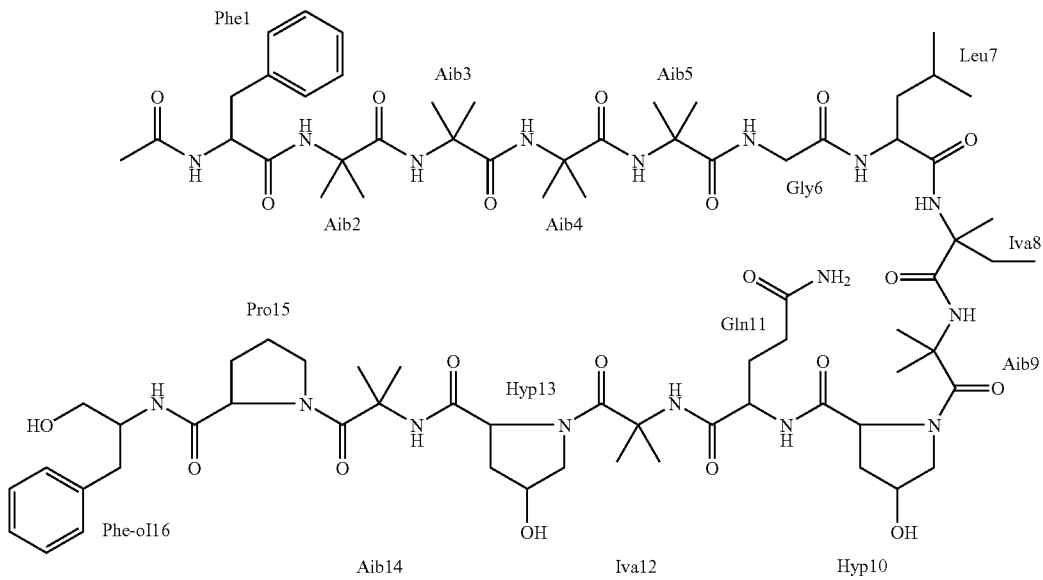

Cephaibol C

Cephaibol D denotes a compound of Formula I in which Xaa$_1$ is Aib, Xaa$_2$ is Gly, Xaa$_3$ and Xaa$_4$ are Aib, and Xaa$_5$ is Phe-ol:

AcPhe-Aib-Aib-Aib-Aib-Gly-Leu-Aib-Aib-Hyp-Gln-Aib-Hyp-Aib-Pro-Xaa$_5$ (SEQ ID NO:5)

Cephaibol D

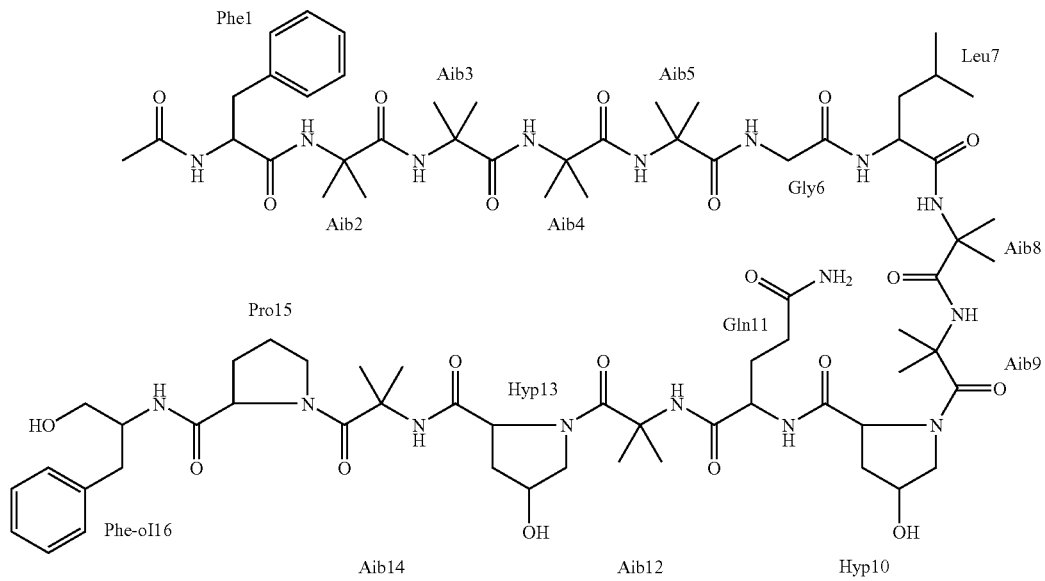

Cephaibol E denotes a compound of Formula I in which Xaa$_1$ is Aib, Xaa$_2$ is Gly, Xaa$_3$ is Aib, Xaa$_4$ is Iva, and Xaa$_5$ is Phe-ol:

AcPhe-Aib-Aib-Aib-Aib-Gly-Leu-Aib-Aib-Hyp-Gln-Iva-Hyp-Aib-Pro-Phe-ol (SEQ ID NO:6)

Cephaibol E

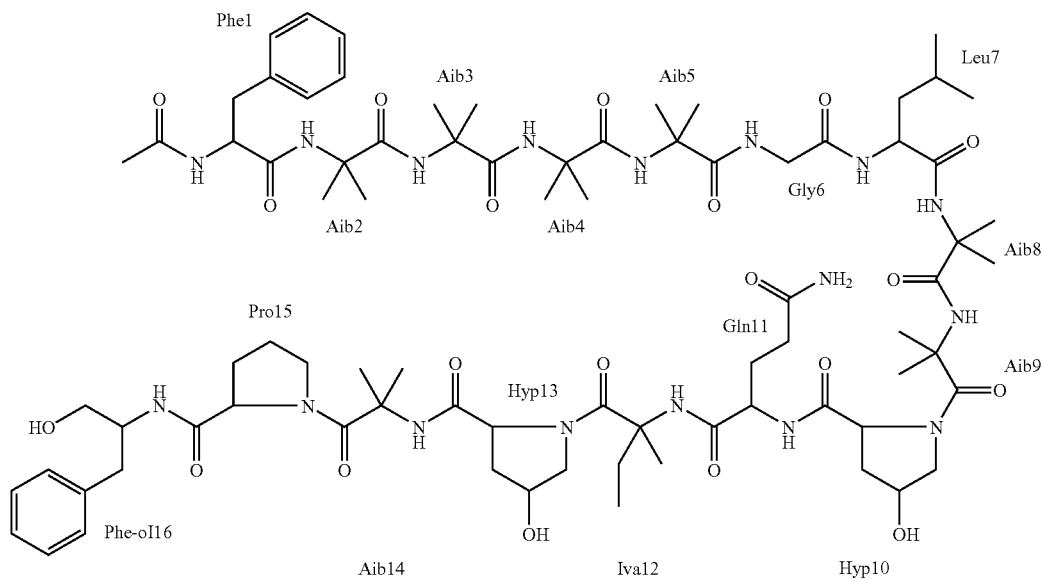

Cephaibol P denotes a compound of Formula II in which Xaa₆ is Hyp:
AcPhe-Iva-Gln-Aib-Ile-Thr-Aib-Leu-Aib-Hyp-Gln-Aib-Hyp-Aib-Pro-Phe-Ser (SEQ ID NO:7)

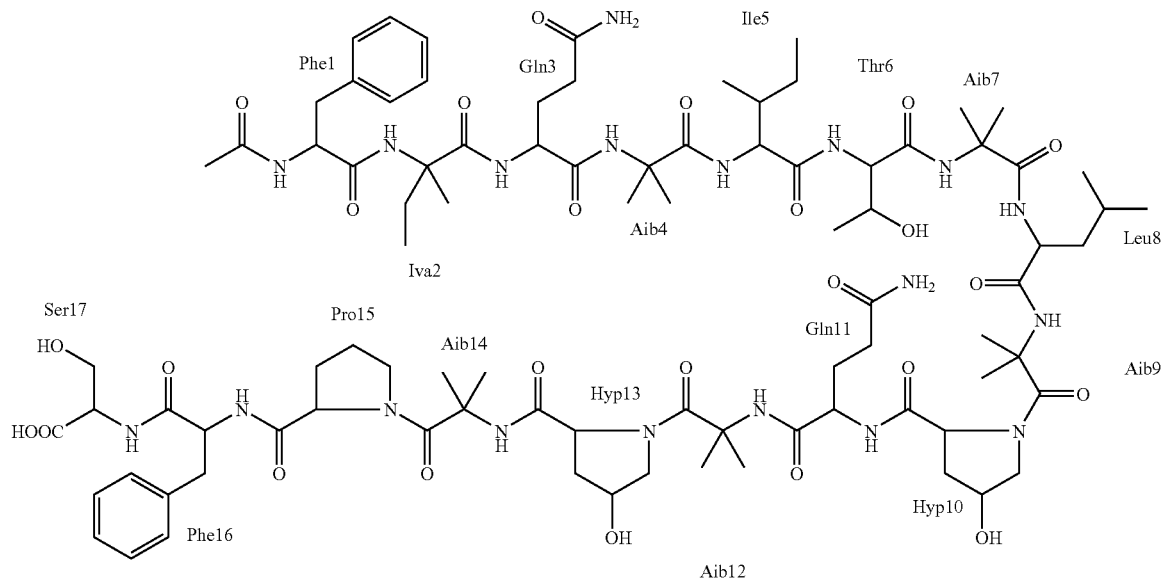

Cephaibol P

Cephaibol Q denotes a compound of Formula II in which Xaa₆ is Pro:
AcPhe-Iva-Gln-Aib-Ile-Thr-Aib-Leu-Aib-Pro-Gln-Aib-Hyp-Aib-Pro-Phe-Ser (SEQ ID NO:8)

U.S. Pat. No. 6,582,949, or in Schiell et al, J. Antibiotics, 54 (2001), 220–233, all of the contents of which are incorporated by reference. The above-described cephaibols can be produced, for example, by the microorganism Acremonium tubakii FH 1685 DSM 12774, with the microorganism being fermented under suitable conditions until the cephaibols accrue in the fermentation medium, and can then be isolated and purified (WO 00/68256; U.S. Pat. No. 6,582,949; Schiell et al, J. Antibiotics, 54 (2001), 220233). An isolate was deposited in the Deutsche Sammlung von Mikroorgan-

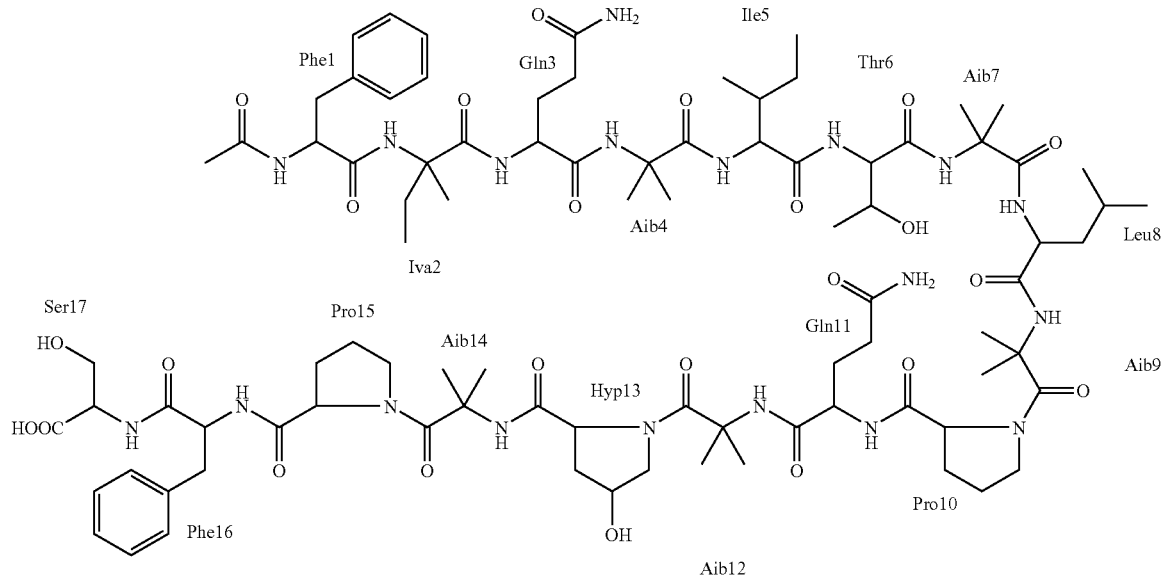

Cephaibol Q

The abovementioned compounds are known and can be prepared, for example, as described in WO 00/68256, in ismen und Zellkulturen (the German Collection of Microorganisms and Cell Cultures) GmbH, Mascheroder Weg 1 B, 038124 Brunswick, Germany, in accordance with the rules of the Budapest treaty of Mar. 31, 1999 under the following number: Acremonium tubakii FH 1685 DSM 12774.

The cephaibols of Formulas I and II may be used in the form of their racemates, racemic mixtures, and pure enantiomers and also their diastereomers and mixtures thereof. Provided the abovementioned compounds permit diastereoisomeric or enantiomeric forms, and accrue as their mixtures in the chosen synthesis, separation into the pure stereoisomers is achieved either by chromatography on an optionally chiral support material or, provided the abovementioned racemic compounds are capable of salt formation, by means of the fractional crystallization of the diastereomeric salts which are formed using an optically active base or acid as auxiliary agent.

The present invention also encompasses the use of obvious chemical equivalents of the compounds of Formulas I or II. Examples of such equivalents are esters, ethers, addition salts, complexes or partial hydrolysis products.

Further equivalents include prodrugs of the compounds of Formulas I and II. "Prodrug," as used here, means a compound which is convertible in vivo by metabolic means (for example, by hydrolysis) to compounds of Formulas I or II. For example, an ester of a compound of Formulas I or II containing a hydroxy group may be convertible by hydrolysis in vivo to the parent molecule. Alternatively, an ester of a compound of Formulas I or II containing a carboxy group may be convertible by hydrolysis in vivo to the parent molecule. Suitable esters of compounds of Formulas I or II containing a hydroxy group, are, for example, acetates, citrates, lactates, tartrates, malonates, oxalates, salicylates, propionates, succinates, fumarates, maleates, methylene-bis-beta-hydroxynaphthoates, gentisates, isethionates, di-p-toluoyltartrates, methanesulphonates, ethanesulphonates, benzenesulphonates, p-toluenesulphonates, cyclohexylsulphamates and quinates.

An especially useful class of esters of compounds of Formulas I or II containing a hydroxy group may be formed from acid moieties selected from those described by Bundgaard et. al., J. Med. Chem., 1989, 32, page 2503–2507, and include substituted (aminomethyl)-benzoates, such as dialkylamino-methylbenzoates in which the two alkyl groups may be joined together and/or interrupted by an oxygen atom or by an optionally substituted nitrogen atom, e.g., an alkylated nitrogen atom, more especially (morpholino-methyl)benzoates, e.g. 3- or 4-(morpholinomethyl) benzoates, and (4-alkylpiperazin-1-yl)benzoates, e.g. 3- or 4-(4-alkylpiperazin-1 yl)benzoates.

The cephaibols of the invention may be administered as physiologically tolerated salts. These salts include organic salts and their inorganic salts, as are described, for example, in Remington's Pharmaceutical Sciences (17th edition, page 1418 (1985)). Because of their physical and chemical stability and their solubility, sodium salts, potassium salts, calcium salts and ammonium salts are preferred for acidic groups; salts of hydrochloric acid, sulfuric acid or phosphoric acid or of carboxylic acids or sulfonic acids, such as acetic acid, citric acid, benzoic acid, maleic acid, fumaric acid, tartaric acid and p-toluenesulfonic acid are preferred for basic groups.

In a preferred embodiment, the cephaibols of the invention are administered as pharmaceutical preparations comprising one or more cephaibol and suitable auxiliary substances or carrier material. Any pharmacologically tolerated carrier materials and/or auxiliary substances can be used as carrier material. Examples of frequently employed carrier substances or auxiliary substances are magnesium carbonate, titanium dioxide, lactose, mannitol and other sugars, talc, milk protein, gelatin, starch, vitamins, cellulose and its derivatives, animal or vegetable oils, polyethylene glycols and solvents, such as sterile water, alcohols, glycerol and polyhydric alcohols.

In general, the pharmaceutical preparations are administered orally, locally, or parenterally, although rectal use is also possible. Examples of suitable solid or liquid galenic preparation forms are granules, powders, tablets, sugar-coated tablets, capsules (including microcapsules), suppositories, syrups, emulsions, suspensions, aerosols, drops or injectable solutions in ampoule form, and preparations providing protracted release of the active compound. Carrier substances, additives, and adjuvants, including, for example, disintegrants, binders, coating agents, swelling agents, ligands, lubricants, flavorings, sweeteners, and solubilizers may also be used.

Where appropriate, the dosage units for oral administration can be microencapsulated in order to delay release or extend it over a relatively long period of time, for example by means of coating or embedding the active compound, in particle form, in suitable polymers, waxes or the like.

The pharmaceutical preparations are preferably produced and administered in dosage units, with each unit containing, as the active constituent, a defined dose of one or more compounds of the cephaibols according to the invention. When administered enterally, such as by tablets, capsules, and suppositories, the dose is about 1 mg to 2000 mg per day, and preferably about 1 to 1000 mg per day. When administered parenterally, such as by injection in ampoule form, the does is about 1 mg to 1000 mg per day, and preferably about 10 mg to 300 mg per day.

The daily dose to be administered depends on the bodyweight, age, sex and condition of the mammal. The daily dose can be administered either once a day, in the form of a single dosage unit, or in smaller dosage units more than once a day, or by administering multiple, subdivided doses at defined intervals.

The cephaibols of the invention may be used to treat any condition in which the normal functioning of the nervous system has been impaired or is desired to be altered. Examples of such conditions include, but are not limited to, those conditions with psychopathological symptoms, such as hallucinations, delusion, psychomotor excitation, schizophrenia, apprehensive agitation, acute manic phases, acute psychotic syndromes, such as paranoid or paranoid-hallucinatory states, and states of anxiety and tension; neurodegenerative diseases, such as Parkinson's disease, Alzheimer's disease, schizophrenia, and depression; and those conditions treated with psychotropic drugs such as neuroleptic agents, antidepressants, and tranquilizers. The function of these drugs is to eliminate or attenuate the psychopathological symptoms: tranquilizers are compounds which mainly have a calming effect on the psyche and which reduce anxiety; antidepressants are substances which improve a pathologically cast-down prevailing mood and are able to eliminate depressive delusions; neuroleptic agents are suitable for calming psychomotor excitation (such as with epilepsy), affective excitability and vigilance and reducing drive, spontaneous movements and expression motoricity.

The cephaibols of the invention may further be used to effect a particular physiological state that depends on the nervous system. Hence, one can use the cephaibols in connection with anesthesia premedication, neuroleptanalgesia, and neuroleptanasthesia, and to prevent vomiting.

The cephaibols of the invention may also be used to suppress the immune system. Hence, they may be used to treat any of those conditions in which immunosuppressants are employed, such as in transplantation medicine or in association with autoimmune conditions. These conditions include, for example, graft rejection and graft-versus-host disease; chronic glomerulonephritis involving nephrotic syndrome; chronic inflammatory intestinal diseases, such as Crohn's disease; myasthenia gravis; autoimmune hepatitis; thrombocytopenic purpura; inflammatory rheumatic diseases, such as dermatomyositis, lupus erythematodes, and rheumatoid arthritis; scleroderma; psoriasis; and alopecia.

The term "treat," as used here, means to deal with medically. It encompasses preventing the onset of a condition or delaying its appearance, as well as ameliorating it or preventing it from worsening. Hence, one need not wait for a condition to appear before administering the compounds of the invention; instead, one can administer them if there is reason to believe that doing so will prevent the onset of a disease or prevent it from reoccurring.

EXAMPLES

The activity of the cephaibols was tested as follows.

Neuroleptic Effect of the Cephaibols in the Mouse Model

A) Influence on Spontaneous Motility

The influence of cephaibols A, B, C, D and E on motoricity in laboratory mice was observed over various periods of time (from 5 min up to 24 hours). Following the intraperitoneal administration of in each case 10 mg/kg of cephaibol A, B, C, D or E, motoricity (climbing) was observed to be impaired, in comparison with the control mice, under the chosen experimental conditions and after differing periods of observation. The observed effects were particularly pronounced after administering cephaibols B and C.

The observed inhibition of motoricity points to the tested cephaibols possessing neuroleptic properties. Fright reactions (noises) were retained, thereby ruling out the possibility of the cephaibols having a narcotic effect in the experimental arrangement.

B) Hypothermia

As compared with the control animals, and under the chosen experimental conditions, the intraperitoneal administration of in each case 10 mg/kg of cephaibol A, B, C or E to laboratory mice produced a marked reduction in body temperature (particularly pronounced in the case of cephaibols B and C) which could be observed over a relatively long period of time and which likewise points to the tested cephaibols possessing neuroleptic properties.

Immunosuppressant Effect in the *Phoma destructiva* Model

The induction of pigment formation in the fungus *Phoma destructiva* is a test model for, inter alia, identifying a potential immunosuppressant effect in test substances. The implementation of the *Phoma destructiva* test has been described by K. Dornberger et al. in J. Antibiotics, §, 977–989, 1995.

The organism *Phoma destructiva* is a fungus which is known to be pathogenic to plants and which grows, in feebly colored colonies, on agar plates which have been inoculated with vegetative mycelium. Cell differentiation processes, which are accompanied by the formation of a pigment and therefore enable cell differentiation to be detected, are initiated under the influence of special inducers. The pigment, which is a melanin-like substance, can be recognized by its color and quantified photometrically or by measuring the zone size. The known immunosuppressant J cyclosporin A gives rise to a morphological change and pigment formation in the test organism.

It has now been found that the cephaibols according to the invention bring about similar pigment formation in *Phoma destructiva* than cyclosporin A does.

Experimental Protocol:

The fungus *Phoma destructiva* was cultured on sloping agar tubes containing culture medium A or B at from 20 to 25° C. and then stored at from 4 to 6° C. and re-inoculated in a 2-year rhythm.

| | |
|---|---|
| Culture medium A: | Malt extract, 40 g/L, |
| | Yeast extract, 4 g/L, |
| | Agar, 15 g/L. |
| Culture medium B: | Potato-glucose agar (E. Merck), 39 g/L. |

Inoculation Culture:

The fungus *Phoma destructiva* was cultured at from 20 to 25° C. for 11 days on medium B in 100 mm diameter petri dishes and, after that, washed off with 10 ml of a sterile 0.9% solution of NaCl. The wash-off can be used for 5 days when stored at 8° C.

Punched-Hole Plate Agar Diffusion Test:

The agar diffusion test method was a modification of the standardized agar diffusion assay described in the European Pharmacopoeia [Deutscher Apothekerverlag Stuttgart, pages 113–118, 1997]: 40 mL of test agar medium were liquefied and brought to a constant temperature of 50° C.; from 8 to 10 mL of the inoculation culture were added under sterile conditions and the mixture was then poured into 150 mm diameter test plates. After the plates had cooled, 12 punched holes of 9 mm in diameter were arranged on the plate using a punching implement [J, V. Benett et al. Appl. Micr. 1.1; 170–177, 1966]. The test holes were loaded with 50JiL of the solution to be tested, with one test hole containing cyclosporin as the control substance (1 μg of cyclosporin A in 50 μL of methanol). The plates which had been prepared in this way were cultured at from 20 to 25° C. for from 4 to 5 days.

Under the above-described test conditions, the cephaibols give rise to pigment formation which resembles the yellow pigmentation induced by cyclosporin A. This effect was particularly pronounced in the case of cephaibols A, B and C.

What is claimed is:

1. A method of treating a mammal with a condition of the nervous system, the method comprising administering to a mammal an effective amount of a compound selected from the group consisting of a) AcPhe-Aib-Aib-Aib-$Xaa_1$-$Xaa_2$-Leu-$Xaa_3$-Aib-Hyp-Gln-$Xaa_4$-Hyp-Aib-Pro-$Xaa_5$ (SEQ ID NO:9), wherein $Xaa_5$ is Phe-ol or Phe-al, and $Xaa_1$, $Xaa_2$, $Xaa_3$, and $Xaa_4$ are as follows:

i) $Xaa_1$ is Aib, $Xaa_2$ is Gly or Ala, and $Xaa_3$ and $Xaa_4$ are Iva;

ii) $Xaa_1$ is Iva, $Xaa_2$ is Gly, and $Xaa_3$ and $Xaa_4$ are Iva;

iii) $Xaa_1$ is Aib, $Xaa_2$ is Gly, $Xaa_3$ is Iva, and $Xaa_4$ is Aib;

iv) $Xaa_1$ is Aib, $Xaa_2$ is Gly, and $Xaa_3$ and $Xaa_4$ are Aib; or v) $Xaa_1$ is Aib, $Xaa_2$ is Gly, $Xaa_3$ is Aib and $Xaa_4$ is Iva;

b) AcPhe-Iva-Gln-Aib-Ile-Thr-Aib-Leu-Aib-$Xaa_6$-Gln-Aib-Hyp-Aib-Pro-Phe-Ser (SEQ ID NO:10), wherein $Xaa_6$ is Hyp or Pro; and c) pharmaceutically acceptable salts of the compounds of a) and b).

2. The method of claim 1, wherein the compound is AcPhe-Aib-Aib-Aib-$Xaa_1$-$Xaa_2$-Leu-$Xaa_3$-Aib-Hyp-Gln-$Xaa_4$-Hyp-Aib-Pro-$Xaa_5$ (SEQ ID NO:11), and $Xaa_5$ is Phe-ol.

3. The method of claim 1, wherein the compound is AcPhe-Aib-Aib-Aib-$Xaa_1$-$Xaa_2$-Leu-$Xaa_3$-Aib-Hyp-Gln-$Xaa_4$-Hyp-Aib-Pro-$Xaa_5$ (SEQ ID NO:12), and $Xaa_1$ is Aib, $Xaa_2$ is Gly or Ala, and $Xaa_3$ and $Xaa_4$ are Iva.

4. The method of claim 1, wherein the compound is AcPhe-Aib-Aib-Aib-$Xaa_1$-$Xaa_2$-Leu-$Xaa_3$-Aib-Hyp-Gln-$Xaa_4$-Hyp-Aib-Pro-$Xaa_5$ (SEQ ID NO:13), and $Xaa_1$ is Iva, $Xaa_2$ is Gly, and $Xaa_3$ and $Xaa_4$ are Iva.

5. The method of claim 1, wherein the compound is AcPhe-Aib-Aib-Aib-$Xaa_1$-$Xaa_2$-Leu-$Xaa_3$-Aib-Hyp-Gln- Xaa₄-Hyp-Aib-Pro-Xaa₅ (SEQ ID NO:14), and Xaa₁ is Aib, Xaa₂ is Gly, Xaa₃ is Iva, and Xaa₄ is Aib.

6. The method of claim 1, wherein the compound is AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:15), and Xaa₁ is Aib, Xaa₂ is Gly, and Xaa₃ and Xaa₄ are Aib.

7. The method of claim 1, wherein the compound is AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:16), and Xaa₁ is Aib, Xaa₂ is Gly, Xaa₃ is Aib and Xaa₄ is Iva.

8. The method of claim 1, wherein the compound is AcPhe-Aib-Aib-Aib-Aib-Gly-Leu-Iva-Aib-Hyp-Gln-Iva-Hyp-Aib-Pro-Phe-ol (SEQ ID NO:1).

9. The method of claim 1, wherein the compound is AcPhe-Aib-Aib-Aib-Aib-Ala-Leu-Iva-Aib-Hyp-Gln-Iva-Hyp-Aib-Pro-Phe-ol (SEQ ID NO:2).

10. The method of claim 1, wherein the compound is AcPhe-Aib-Aib-Aib-Iva-Gly-Leu-Iva-Aib-Hyp-Gln-Iva-Hyp-Aib-Pro-Phe-ol (SEQ ID NO:3).

11. The method of claim 1, wherein the compound is AcPhe-Aib-Aib-Aib-Aib-Gly-Leu-Iva-Aib-Hyp-Gln-Aib-Hyp-Aib-Pro-Phe-ol (SEQ ID NO:4).

12. The method of claim 1, wherein the compound is AcPhe-Aib-Aib-Aib-Aib-Gly-Leu-Aib-Aib-Hyp-Gln-Aib-Hyp-Aib-Pro-Phe-ol (SEQ ID NO:5).

13. The method of claim 1, wherein the compound is AcPhe-Aib-Aib-Aib-Aib-Gly-Leu-Aib-Aib-Hyp-Gln-Iva-Hyp-Aib-Pro-Phe-ol (SEQ ID NO:6).

14. The method of claim 1, wherein the compound is AcPhe-Iva-Gln-Aib-Ile-Thr-Aib-Leu-Aib-Hyp-Gln-Aib-Hyp-Aib-Pro-Phe-Ser (SEQ ID NO:17).

15. The method of claim 1, wherein the compound is AcPhe-Iva-Gln-Aib-Ile-Thr-Aib-Leu-Aib-Pro-Gln-Aib-Hyp-Aib-Pro-Phe-Ser (SEQ ID NO:18).

16. The method of claim 1, wherein the compound is administered in an amount of between about 1 mg and 1000 mg per day.

17. The method of claim 1, wherein the condition is selected from the group consisting of hallucinations, delusion, psychomotor excitation, schizophrenia, apprehensive agitation, acute manic phases, acute psychotic syndromes, anxiety, tension, neurodegenerative diseases, anesthesia, neuroleptanalgesia, neuroleptanasthesia, and vomiting.

18. The method of claim 1, wherein the compound further includes a pharmaceutically acceptably carrier.

19. A method of treating a mammal with a condition of the nervous system, the method comprising administering to a mammal an effective amount of a compound selected from the group consisting of
    a) a prodrug of AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:9),
        wherein Xaa₅ is Phe-ol or Phe-al, and Xaa₁, Xaa₂, Xaa₃, and Xaa₄ are as follows:
        i) Xaa₁ is Aib, Xaa₂ is Gly or Ala, and Xaa₃ and Xaa₄ are Iva;
        ii) Xaa₁ is Iva, Xaa₂ is Gly, and Xaa₃ and Xaa₄ are Iva;
        iii) Xaa₁ is Aib, Xaa₂ is Gly, Xaa₃ is Iva, and Xaa₄ is Aib;
        iv) Xaa₁ is Aib, Xaa₂ is Gly, and Xaa₃ and Xaa₄ are Aib; or
        v) Xaa₁ is Aib, Xaa₂ is Gly, Xaa₃ is Aib and Xaa₄ is Iva;
    b) a prodrug of AcPhe-Iva-Gln-Aib-Ile-Thr-Aib-Leu-Aib-Xaa₆-Gln-Aib-Hyp-Aib-Pro-Phe-Ser (SEQ ID NO:10), wherein Xaa₆ is Hyp or Pro; and
    c) pharmaceutically acceptable salts of the compounds of a) and b).

20. The method of claim 19, wherein the compound is a prodrug of AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:11), and Xaa₁ is Phe-ol.

21. The method of claim 19, wherein the compound is a prodrug of AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:12), and Xaa₁ is Aib, Xaa₂ is Gly or Ala, and Xaa₃ and Xaa₄ are Iva.

22. The method of claim 19, wherein the compound is a prodrug of AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:13), and Xaa₁ is Iva, Xaa₂ is Gly, and Xaa₃ and Xaa₄ are Iva.

23. The method of claim 19, wherein the compound is a prodrug of AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:14), and Xaa₁ is Aib, Xaa₂ is Gly, Xaa₃ is Iva, and Xaa₄ is Aib.

24. The method of claim 19, wherein the compound is a prodrug of AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:15), and Xaa₁ is Aib, Xaa₂ is Gly, and Xaa₃ and Xaa₄ are Aib.

25. The method of claim 19, wherein the compound is a prodrug of AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:16), and Xaa₁ is Aib, Xaa₂ is Gly, Xaa₃ is Aib and Xaa₄ is Iva.

26. The method of claim 19, wherein the compound is AcPhe-Aib-Aib-Aib-Aib-Gly-Leu-Iva-Aib-Hyp-Gln-Iva-Hyp-Aib-Pro-Phe-ol (SEQ ID NO:1).

27. The method of claim 19, wherein the compound is AcPhe-Aib-Aib-Aib-Aib-Ala-Leu-Iva-Aib-Hyp-Gln-Iva-Hyp-Aib-Pro-Phe-ol (SEQ ID NO:2).

28. The method of claim 19, wherein the compound is AcPhe-Aib-Aib-Aib-Iva-Gly-Leu-Iva-Aib-Hyp-Gln-Iva-Hyp-Aib-Pro-Phe-ol (SEQ ID NO:3).

29. The method of claim 19, wherein the compound is AcPhe-Aib-Aib-Aib-Aib-Gly-Leu-Iva-Aib-Hyp-Gln-Aib-Hyp-Aib-Pro-Phe-ol (SEQ ID NO:4).

30. The method of claim 19, wherein the compound is AcPhe-Aib-Aib-Aib-Aib-Gly-Leu-Aib-Aib-Hyp-Gln-Aib-Hyp-Aib-Pro-Phe-ol (SEQ ID NO:5).

31. The method of claim 19, wherein the compound is AcPhe-Aib-Aib-Aib-Aib-Gly-Leu-Aib-Aib-Hyp-Gln-Iva-Hyp-Aib-Pro-Phe-ol (SEQ ID NO:6).

32. The method of claim 19, wherein the compound is AcPhe-Iva-Gln-Aib-Ile-Thr-Aib-Leu-Aib-Hyp-Gln-Aib-Hyp-Aib-Pro-Phe-Ser (SEQ ID NO:17).

33. The method of claim 19, wherein the compound is AcPhe-Iva-Gln-Aib-Ile-Thr-Aib-Leu-Aib-Pro-Gln-Aib-Hyp-Aib-Pro-Phe-Ser (SEQ ID NO:18).

34. The method of claim 19, wherein the compound is administered in an amount of between about 1 mg and 1000 mg per day.

35. The method of claim 19, wherein the condition is selected from the group consisting of hallucinations, delusion, psychomotor excitation, schizophrenia, apprehensive agitation, acute manic phases, acute psychotic syndromes, anxiety, tension, neurodegenerative diseases, anesthesia, neuroleptanalgesia, neuroleptanasthesia, and vomiting.

36. A method of suppressing an immune response in a mammal in need of immunosuppression, the method comprising administering to a mammal an effective amount of a compound selected from the group consisting of
    a) AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:9),
        wherein Xaa₅ is Phe-ol or Phe-al, and Xaa₁, Xaa₂, Xaa₃, and Xaa₄ are as follows:
        i) Xaa₁ is Aib, Xaa₂ is Gly or Ala, and Xaa₃ and Xaa₄ are Iva;

ii) Xaa₁ is Iva, Xaa₂ is Gly, and Xaa₃ and Xaa₄ are Iva;
iii) Xaa₁ is Aib, Xaa₂ is Gly, Xaa₃ is Iva, and Xaa₄ is Aib;
iv) Xaa₁ is Aib, Xaa₂ is Gly, and Xaa₃ and Xaa₄ are Aib; or
v) Xaa₁ is Aib, Xaa₂ is Gly, Xaa₃ is Aib and Xaa₄ is Iva;
b) AcPhe-Iva-Gln-Aib-Ile-Thr-Aib-Leu-Aib-Xaa₆-Gln-Aib-Hyp-Aib-Pro-Phe-Ser (SEQ ID NO:10), wherein Xaa₆ is Hyp or Pro; and
c) pharmaceutically acceptable salts of the compounds of a) and b).

37. The method of claim 36, wherein the compound is AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:11), and Xaa₅ is Phe-ol.

38. The method of claim 36, wherein the compound is AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:12), and Xaa₁ is Aib, Xaa₂ is Gly or Ala, and Xaa₃ and Xaa₄ are Iva.

39. The method of claim 36, wherein the compound is AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:13), and Xaa₁ is Iva, Xaa₂ is Gly, and Xaa₃ and Xaa₄ are Iva.

40. The method of claim 36, wherein the compound is AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:14), and Xaa₁ is Aib, Xaa₂ is Gly, Xaa₃ is Iva, and Xaa₄ is Aib.

41. The method of claim 36, wherein the compound is AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:15), and Xaa₁ is Aib, Xaa₂ is Gly, and Xaa₃ and Xaa₄ are Aib.

42. The method of claim 36, wherein the compound is AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:16), and Xaa₁ is Aib, Xaa₂ is Gly, Xaa₃ is Aib and Xaa₄ is Iva.

43. The method of claim 36, wherein the compound is AcPhe-Aib-Aib-Aib-Aib-Gly-Leu-Iva-Aib-Hyp-Gln-Iva-Hyp-Aib-Pro-Phe-ol (SEQ ID NO:1).

44. The method of claim 36, wherein the compound is AcPhe-Aib-Aib-Aib-Aib-Ala-Leu-Iva-Aib-Hyp-Gln-Iva-Hyp-Aib-Pro-Phe-ol (SEQ ID NO:2).

45. The method of claim 36, wherein the compound is AcPhe-Aib-Aib-Aib-Iva-Gly-Leu-Iva-Aib-Hyp-Gln-Iva-Hyp-Aib-Pro-Phe-ol (SEQ ID NO:3).

46. The method of claim 36, wherein the compound is AcPhe-Aib-Aib-Aib-Aib-Gly-Leu-Iva-Aib-Hyp-Gln-Aib-Hyp-Aib-Pro-Phe-ol (SEQ ID NO:4).

47. The method of claim 36, wherein the compound is AcPhe-Aib-Aib-Aib-Aib-Gly-Leu-Aib-Aib-Hyp-Gln-Aib-Hyp-Aib-Pro-Phe-ol (SEQ ID NO:5).

48. The method of claim 36, wherein the compound is AcPhe-Aib-Aib-Aib-Aib-Gly-Leu-Aib-Aib-Hyp-Gln-Iva-Hyp-Aib-Pro-Phe-ol (SEQ ID NO:6).

49. The method of claim 36, wherein the compound is AcPhe-Iva-Gln-Aib-Ile-Thr-Aib-Leu-Aib-Hyp-Gln-Aib-Hyp-Aib-Pro-Phe-Ser (SEQ ID NO:17).

50. The method of claim 36, wherein the compound is AcPhe-Iva-Gln-Aib-Ile-Thr-Aib-Leu-Aib-Pro-Gln-Aib-Hyp-Aib-Pro-Phe-Ser (SEQ ID NO:18).

51. The method of claim 36, wherein the compound is administered in an amount of between about 1 mg and 1000 mg per day.

52. The method of claim 36, wherein the compound is administered to treat a disease selected from the group consisting of graft rejection, graft-versus-host disease, chronic glomerulonephritis, Crohn's disease, myasthenia gravis, autoimmune hepatitis, thrombocytopenic purpura, dermatomyositis, lupus erythematodes, rheumatoid arthritis, scleroderma, psoriasis, and alopecia diseases.

53. The method of claim 36, wherein the compound further includes a pharmaceutically acceptably carrier.

54. A method of suppressing an immune response in a mammal in need of immunosuppression, the method comprising administering to a mammal an effective amount of a compound selected from the group consisting of
a) a prodrug of AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:9),
  wherein Xaa₅ is Phe-ol or Phe-al, and Xaa₁, Xaa₂, Xaa₃, and Xaa₄ are as follows:
  a) Xaa₁ is Aib, Xaa₂ is Gly or Ala, and Xaa₃ and Xaa₄ are Iva;
  b) Xaa₁ is Iva, Xaa₂ is Gly, and Xaa₃ and Xaa₄ are Iva;
  c) Xaa₁ is Aib, Xaa₂ is Gly, Xaa₃ is Iva, and Xaa₄ is Aib;
  d) Xaa₁ is Aib, Xaa₂ is Gly, and Xaa₃ and Xaa₄ are Aib; or
  e) Xaa₁ is Aib, Xaa₂ is Gly, Xaa₃ is Aib and Xaa₄ is Iva;
b) a prodrug of AcPhe-Iva-Gln-Aib-Ile-Thr-Aib-Leu-Aib-Xaa₆-Gln-Aib-Hyp-Aib-Pro-Phe-Ser (SEQ ID NO:10), wherein Xaa₆ is Hyp or Pro; and
c) pharmaceutically acceptable salts of the compounds of a) and b).

55. The method of claim 54, wherein the compound is a prodrug of AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:11), and Xaa₅ is Phe-ol.

56. The method of claim 54, wherein the compound is a prodrug of AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:12), and Xaa₁ is Aib, Xaa₂ is Gly or Ala, and Xaa₃ and Xaa₄ are Iva.

57. The method of claim 54, wherein the compound is a prodrug of AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:13), and Xaa₁ is Iva, Xaa₂ is Gly, and Xaa₃ and Xaa₄ are Iva.

58. The method of claim 54, wherein the compound is a prodrug of AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:14), and Xaa₁ is Aib, Xaa₂ is Gly, Xaa₃ is Iva, and Xaa₄ is Aib.

59. The method of claim 54, wherein the compound is a prodrug of AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:15), and Xaa₁ is Aib, Xaa₂ is Gly, and Xaa₃ and Xaa₄ are Aib.

60. The method of claim 54, wherein the compound is a prodrug of AcPhe-Aib-Aib-Aib-Xaa₁-Xaa₂-Leu-Xaa₃-Aib-Hyp-Gln-Xaa₄-Hyp-Aib-Pro-Xaa₅ (SEQ ID NO:16), and Xaa₁ is Aib, Xaa₂ is Gly, Xaa₃ is Aib and Xaa₄ is Iva.

61. The method of claim 54, wherein the compound is AcPhe-Aib-Aib-Aib-Aib-Gly-Leu-Iva-Aib-Hyp-Gln-Iva-Hyp-Aib-Pro-Phe-ol (SEQ ID NO:1).

62. The method of claim 54, wherein the compound is AcPhe-Aib-Aib-Aib-Aib-Ala-Leu-Iva-Aib-Hyp-Gln-Iva-Hyp-Aib-Pro-Phe-ol (SEQ ID NO:2).

63. The method of claim 54, wherein the compound is AcPhe-Aib-Aib-Aib-Iva-Gly-Leu-Iva-Aib-Hyp-Gln-Iva-Hyp-Aib-Pro-Phe-ol (SEQ ID NO:3).

64. The method of claim 54, wherein the compound is AcPhe-Aib-Aib-Aib-Aib-Gly-Leu-Iva-Aib-Hyp-Gln-Aib-Hyp-Aib-Pro-Phe-ol (SEQ ID NO:4).

65. The method of claim 54, wherein the compound is AcPhe-Aib-Aib-Aib-Aib-Gly-Leu-Aib-Aib-Hyp-Gln-Aib-Hyp-Aib-Pro-Phe-ol (SEQ ID NO:5).

66. The method of claim 54, wherein the compound is AcPhe-Aib-Aib-Aib-Aib-Gly-Leu-Aib-Aib-Hyp-Gln-Iva-Hyp-Aib-Pro-Phe-ol (SEQ ID NO:6).

67. The method of claim 54, wherein the compound is AcPhe-Iva-Gln-Aib-Ile-Thr-Aib-Leu-Aib-Hyp-Gln-Aib-Hyp-Aib-Pro-Phe-Ser (SEQ ID NO:17).

68. The method of claim 54, wherein the compound is AcPhe-Iva-Gln-Aib-Ile-Thr-Aib-Leu-Aib-Pro-Gln-Aib-Hyp-Aib-Pro-Phe-Ser (SEQ ID NO:18).

69. The method of claim 54, wherein the compound is administered in an amount of between about 1 mg and 1000 mg per day.

70. The method of claim 54, wherein the compound is administered to treat a disease selected from the group consisting of graft rejection, graft-versus-host disease, chronic glomerulonephritis, Crohn's disease, myasthenia gravis, autoimmune hepatitis, thrombocytopenic purpura, dermatomyositis, lupus erythematodes, rheumatoid arthritis, scleroderma, psoriasis, and alopecia.

71. The method of claim 54, wherein the compound further includes a pharmaceutically acceptably carrier.

* * * * *